United States Patent [19]

Larock et al.

[11] Patent Number: 4,879,426

[45] Date of Patent: Nov. 7, 1989

[54] PALLADIUM-CATALYZED ARYLATION OF CYCLOALKENES

[75] Inventors: Richard C. Larock; Bruce E. Baker, both of Ames, Iowa

[73] Assignee: Iowa State University Research Foundation, Inc., Ames, Iowa

[21] Appl. No.: 191,896

[22] Filed: May 9, 1988

[51] Int. Cl.$^4$ .............................................. C07C 1/20
[52] U.S. Cl. ..................................... 585/469; 585/434
[58] Field of Search .............................. 585/469, 434

[56] References Cited

U.S. PATENT DOCUMENTS

| | | | |
|---|---|---|---|
| 2,691,686 | 10/1954 | Bloch | 260/619 |
| 3,082,268 | 3/1963 | McNelis | 260/668 |
| 3,251,895 | 5/1966 | Wilkes | 260/668 |
| 3,595,931 | 7/1971 | Hay et al. | 585/469 |
| 3,767,714 | 10/1973 | Kominami | 260/650 R |
| 4,117,019 | 9/1978 | Eiingsfeld | 260/649 R |
| 4,228,313 | 10/1980 | Cardenas et al. | 585/640 |
| 4,251,675 | 2/1981 | Engel | 585/469 |
| 4,632,996 | 12/1986 | Larock et al. | 549/209 |

OTHER PUBLICATIONS

Chemical Abstracts, 99:70299x (1983).
Chemical Abstracts, 101:72454c (1984).
Chemical Abstracts, 102:4857a (1985).

*Primary Examiner*—H. M. S. Sneed
*Assistant Examiner*—Chung K. Pak
*Attorney, Agent, or Firm*—Zarley, McKee, Thomte, Voorhees & Sease

[57] ABSTRACT

A direct coupling reaction which goes in high yields to couple an aryl halide with a cycloalkene.

16 Claims, No Drawings

PALLADIUM-CATALYZED ARYLATION OF CYCLOALKENES

BACKGROUND OF THE INVENTION

The coupling reaction of alkyl halides and Grignard reagents have been known for sometime. However, to couple aryl halides and cycloalkenes has not proven easy. In particular, the reactions for coupling aryl halides and cycloalkenes have been known to be slow, low in selectivity and are known to produce the desired product in low yields at best. Reactions which are known to produce coupling between an aryl halide and a cycloalkene, such as modifications of the Heck palladium-catalyzed cross-coupling of aryl halides and acyclic alkenes, in the past have employed elevated temperatures, tend to generate isomeric mixtures and are difficult to control and even then frequently provide low yields.

There is a real need for a direct coupling reaction between aryl halides and cycloalkenes to provide aromatic compounds with at least one of the nuclear hydrogen atoms replaced by an unsaturated cyclic hydrocarbon group. Such compounds are known to be useful as chemical intermediates in synthesis of wetting agents, detergents, bactericides, insecticides, resins and other organic compounds, as well. They are, in short, compounds of active interest. See, for example, U.S. Pat. No. 2,691,686 which issued Oct. 12, 1954, Bloch for Condensation of Aromatic Compounds with Cyclic Polyolefins. Also, for some of the difficulties of coupling reactions involving Grignard reagents and allylic halides see Cardenas U.S. Pat. No. 4,228,313 issued Oct. 14, 1980.

In accordance with the primary objective of the present invention, a mild, catalytic arylation of cycloalkenes is performed. This reaction is of considerable use in synthetic organic chemistry, as earlier outlined.

An additional object of the present invention is to provide such a reaction as above described which goes under mild conditions and provides a high yield of reaction product, generally in excess of 75% and at times in nearly quantitative yield.

SUMMARY OF THE INVENTION

A method of providing high yield arylation of cycloalkenes by a direct coupling reaction between an aryl halide and a cycloalkene in the presence of a palladium(II) ion source and an alkali metal salt, with the reaction occurring in the presence of a yield-enhancing organic solvent.

DETAILED DESCRIPTION OF THE INVENTION

An illustrative reaction of the present invention may be illustrated by the following coupling equation.

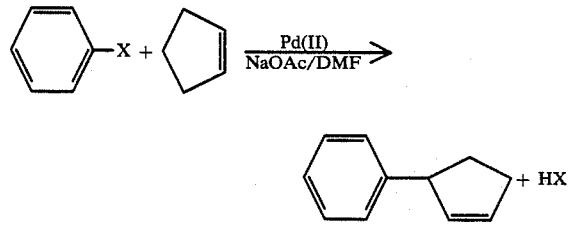

In this reaction it can be seen that the aryl halide is preferably a phenyl halide. X represents the halide moiety and it can be chloride, bromide or iodide.

The cycloalkene that is illustrated is cyclopentene. However, as illustrated by the examples below, it is not critical that the cycloalkene be cyclopentene. It can be any ring size, but preferably $C_5$ through $C_8$ ring size cycloalkenes. In short, in the preferred embodiment it can be cyclopentene, cyclohexene, cycloheptene, and cyclooctene.

In order to make the reaction go, the reaction must be promoted by a source of palladium(O) or palladium(II) ion. The precise source is not critical. The preferred palladium(O) source is tetrakis-(triphenylphosphine)-palladium(O). Preferably where the salt is a palladium(II) salt, it is a palladium(II) water soluble salt and is palladium acetate. However, it may also be conducted in the presence of palladium chloride and other palladium water soluble salts as well. The amount of palladium present is an amount sufficient to effectively promote the direct coupling reaction and catalytically effective amounts work. Generally, the amount should be from about 0.5 mole percent of the initial reactants up to about 5.0 mole percent of the initial reactants, with a preferred amount being from about 1.5 to 3%.

Preferably the reaction is conducted in the presence of a reaction-promoting effective amount of an alkali metal salt. Most preferably the salt has the same anion as the palladium(II) ion source. Thus, for example if the palladium(II) ion source is acetate, it is preferred that the alkali metal salt also be an acetate. Suitable alkali metals are sodium, potassium and cesium. Generally, the most satisfactory results are with potassium salts, from the standpoint that they seem to give the highest yields. Likewise, it is preferred that the cycloalkene be cyclopentene because it gives higher yields and faster reactions.

The amount of the added salt may vary from about 0.5 equivalents up to about 3 equivalents of alkali metal salt. Also, mixtures of sodium, potassium and cesium salts may be employed as well. It has been found preferable to use a molar excess, perhaps up to 3 equivalents of the added alkali metal salt.

It has been found that yields are significantly increased if the reaction is run in the presence of a yield-enhancing organic solvent. The most preferred solvent is N,N-dimethylformamide (DMF). Other suitable polar solvents may be used as well, such as tetrahydrofuran, methyl alcohol, diethyl ether, hexamethylphosphoramide, acetonitrile and the like.

The temperatures at which the reaction is run is not critical. Indeed, it is one of the advantages of the invention that it can be run at room temperature. Generally speaking, temperatures of from 0° C. up to 80° C. can be used, though higher temperatures can certainly be employed effectively. Likewise, the reaction does not appear to be particularly time-dependent, and satisfactory times can range from 0.5 hours up to 72 hours, with a typical reaction going to completion within 12–48 hours.

It is also preferred in the reaction that the amount of the cycloalkene be in excess of an equimolar amount, perhaps up to 4 equivalents in excess.

Alkali metal acetates in DMF have proven superior to all other combinations examined, including carbonate bases and triethylamine, although these also work well. Using 2.5% $Pd(OAc)_2$, three equivalents of KOAc, five equivalents of cyclopentene and one equivalent of n-

Bu₄NCl in DMF at room temperature, it has been possible to prepare 3-phenylcyclopentene in quantitative yield. While generally an excess of the readily available cycloalkene has been used, one can employ lesser amounts with satisfactory results. For example, iodobenzene and 1.5 equivalents of cyclopentene afforded an 81% yield of allylic product in only 12 hours at room temperature.

As illustrated in the examples, these reactions are preferably conducted in the presence of tetra-n-butylammonium chloride, generally one equivalent. This is not essential but preferred for increased rate of reaction for increased yield, and to allow the reaction to go at mild temperatures. Other tetraalkylammonium or tetraalkylphosphonium halide salts may be used as well.

EXAMPLES

The examples of 1-11 of this invention are summarized in the table below. These reaction conditions have proven effective for the cross-coupling of a wide variety of aryl halides and cycloalkenes as summarized in the examples in Table I. Cycloalkenes of ring size 5 through 8 are readily accommodated (entries 1-5), but cyclohexene gave a higher yield when NaOAc was used as the base (entry 2) and cyclooctene gave a cleaner reaction with CsOAc as the base (entry 4). Most surprising was the observation that cycloheptene gave the homoallylic isomer, 4-phenylcycloheptene, exclusively (entry 3). Under identical reaction conditions (KOAc as base) the following relative reactivities of the cycloalkenes were observed: cyclopentene >cyclooctene >cycloheptene >cyclohexene.

A variety of aryl halides can be successfully employed in these arylation reactions. Electron-withdrawing substituents, whether in the ortho or para positions, do not particularly deactivate the arene towards substitution (entries 6-9), but electron-donating groups slow the reaction and tend to require slightly higher reaction temperatures (entries 10, 11). On the other hand, it has been found that nitro groups are incompatible with the reaction. While phenyl bromide has proven virtually inert under these reaction conditions, aryl bromides bearing electron-withdrawing groups (entry 9) can be employed.

It is important to note that these reactions can be scaled up with only a slight increase in reaction time or temperature being necessary to complete the reaction. For example, 3-phenylcyclopentene can be prepared on a 50 mmol scale in 87% distilled yield when the reaction of phenyl iodide and cyclopentene is run for 3.5 days at room temperature. Similarly, ethyl o-iodobenzoate and cyclopentene afford the cross-coupled product in 90% distilled yield when run on a 10 mmol scale.

It is evident that this mild catalytic arylation process should find considerable application in organic synthesis.

TABLE I

Palladium-Catalyzed Intermolecular Arylation of Cycloalkenes[a]

| entry | aryl halide | cycloalkene | base | reaction conditions | product | % yield[b] |
|---|---|---|---|---|---|---|
| 1 | PhI | cyclopentene | KOAc | 2 d, 25° C. | 3-phenylcyclopentene | 100(89) |
| 2 | PhI | cyclohexene | NaOAc | 5 d, 25° C. | 3-phenylcyclohexene | 88(70) |
| 3 | PhI | cycloheptene | KOAc | 6 d, 25° C. | 4-phenylcycloheptene | 99(95) |
| 4 | PhI | cyclooctene | CsOAc | 2 d, 25° C. | 3-phenylcyclooctene | 100(85) |
| 5 | PhI | 2,5-dihydrofuran | NaOAc | 4 d, 25° C. | 2-phenyl-2,5-dihydrofuran | 91(78) |
| 6 | ethyl o-iodobenzoate | cyclopentene | KOAc | 0.5 d, 25° C. | ethyl o-(cyclopent-2-enyl)benzoate | 77(74) |

TABLE I-continued
Palladium-Catalyzed Intermolecular Arylation of Cycloalkenes[a]

| entry | aryl halide | cycloalkene | base | reaction conditions | product | % yield[b] |
|---|---|---|---|---|---|---|
| 7 | EtO$_2$C—C$_6$H$_4$—I | | | 3.5 d, 25° C. | EtO$_2$C—C$_6$H$_4$—cyclopentenyl | 90(85) |
| 8 | CH$_3$CO—C$_6$H$_4$—I | | | 4.5 d, 25° C. | CH$_3$CO—C$_6$H$_4$—cyclopentenyl | 96(94) |
| 9 | CH$_3$CO—C$_6$H$_4$—Br | | | 2 d, 80° C. | CH$_3$CO—C$_6$H$_4$—cyclopentenyl | 87 |
| 10 | 2-OCH$_3$-C$_6$H$_4$—I | | | 1 d, 80° C. | 2-OCH$_3$-C$_6$H$_4$—cyclopentenyl | (78) |
| 11 | CH$_3$CO—C$_6$H$_4$—I | | | 3 d, 80° C. | CH$_3$CO—C$_6$H$_4$—cyclohexenyl | (67) |

[a]ArX (0.5 mmol), cycloalkene (2.5 mmol), Pd(OAc)$_2$ (2.5%), n-Bu$_4$NCl (0.5 mmol), base (1.5 mmol), DMF (1 ml).
[b]Yield by gas chromatographic analysis (isolated yield).

It can be seen that the invention accomplishes at least all of its stated objectives.

What is claimed is:

1. A method of high yield arylation of cycloalkenes, comprising:
   (a) reacting an aryl halide with a cycloalkene in the presence of a small but reaction promoting effective amount of a palladium(O) source or a palladium(II) ion source, and an alkali metal salt;
   (b) said reaction occurring in a reaction yield enhancing polar organic solvent.

2. The process of claim 1 wherein said halide is selected from:

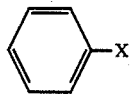

wherein X is selected from the group consisting of chloride, bromide and iodide.

3. The process of claim 1 wherein said cycloalkene is selected from the group of C$_5$ to C$_8$ ring size cycloalkenes.

4. The process of claim 1 wherein said alkali metal salt is an alkali metal acetate.

5. The process of claim 4 wherein said alkali metal is sodium.

6. The process of claim 4 wherein said alkali metal is potassium.

7. The process of claim 4 wherein said alkali metal is cesium.

8. The process of claim 3 wherein the cycloalkene is a C$_5$ cycloalkene.

9. The process of claim 3 wherein the cycloalkene is a C$_6$ cycloalkene.

10. The process of claim 3 wherein the cycloalkene is a C$_7$ cycloalkene.

11. The process of claim 3 wherein the cycloalkene is a C$_8$ cycloalkene.

12. The process of claim 1 wherein said aryl halide is a functionally substituted aryl halide.

13. The reaction of claim 1 wherein the organic solvent is selected from the group consisting of tetrahydrofuran, methyl alcohol, diethyl ether, hexamethylphosphoramide, acetonitrile and dimethylformamide.

14. The reaction of claim 1 wherein the reaction is conducted at a temperature of from 20° C. to 80° C. for from 0.5 to 72.0 hours.

15. The reaction of claim 1 wherein the amount of cycloalkene is in excess of an equimolar amount.

16. The method of claim 1 wherein said reaction is conducted in the presence of tetra-n-butyl-ammonium choloride.